United States Patent [19]
Johnson et al.

[11] Patent Number: 5,944,695
[45] Date of Patent: Aug. 31, 1999

[54] MULTIPLE SHEATH CATHETER USING MULTIPLE STAGES AND METHOD OF USE

[75] Inventors: Steven W. Johnson, West Jordan; Bryan G. Davis, Sandy, both of Utah

[73] Assignee: Becton, Dickinson and Company, Franklin Lakes, N.J.

[21] Appl. No.: 08/941,443

[22] Filed: Sep. 30, 1997

[51] Int. Cl.$^6$ .................................................. A61M 25/00
[52] U.S. Cl. ..................... 604/164; 604/168; 604/171; 604/177
[58] Field of Search .................................. 604/164–171, 604/177, 53, 49, 52, 264

[56] References Cited

U.S. PATENT DOCUMENTS

| | | | |
|---|---|---|---|
| 4,177,809 | 12/1979 | Moorehead | 128/214.4 |
| 4,306,562 | 12/1981 | Osborne | 128/348 |
| 4,886,500 | 12/1989 | Lazarus | 604/164 |
| 5,209,735 | 5/1993 | Lazarus | 604/164 |
| 5,221,263 | 6/1993 | Sinko et al. | 604/161 |
| 5,267,971 | 12/1993 | Brimhall | 604/177 |
| 5,304,144 | 4/1994 | Brimhall | 604/177 |
| 5,356,390 | 10/1994 | Erskine | 604/164 |
| 5,366,441 | 11/1994 | Crawford | 604/53 |
| 5,385,554 | 1/1995 | Brimhall | 604/168 |
| 5,743,882 | 4/1998 | Luther | 604/168 |

*Primary Examiner*—John D. Yasko

[57] ABSTRACT

A multiple sheath catheter is provided for placing an IV catheter or other medical instrument into a blood vessel of a patient. The multiple sheath catheter includes a first stage catheter having a distal end for introducing into a blood vessel, a proximal end, and an internal lumen between the distal and proximal ends. Disposed lengthwise within the lumen of the first stage catheter is a needle for piercing a blood vessel of a patient. The device uses a small diameter needle to gain venous access, thereby reducing the probability of failure. The multiple sheath catheter also includes a second stage catheter or introducer.

16 Claims, 4 Drawing Sheets

MULTIPLE SHEATH CATHETER USING MULTIPLE STAGES AND METHOD OF USE

BACKGROUND

1. The Field of the Invention

The present invention is related generally to the field of medical catheters. More specifically, the present invention relates to a multiple sheath catheter for use in placing an intravenous (IV) catheter or other medical instrument into a blood vessel of a patient.

2. Technical Background

During medical treatment, patients often require medication, blood, or fluids. The most efficient way of administering these substances is by depositing them directly into the patient's blood stream where the circulatory system quickly directs the substance to the target tissue or organ. Thus, vascular catheters for infusion of fluids, blood, and medications into patients are among the most commonly used medical devices. The insertion of a vascular catheter allows repeated or continuous access to the circulatory system of a patient. Vascular catheters are generally inserted into the extremities of a patient and fluids, blood, and medications are provided to the patient through such catheters.

Catheters of this type are generally inserted into a vein or artery by means of an introducer needle. In one common configuration, the catheter is initially placed over the needle. The needle, with the catheter located over the needle, is inserted into the patient until the desired vein or artery is located. Once the needle and catheter are properly located in the vein or artery, the needle is withdrawn from the catheter and discarded. The catheter remains in the vein or artery to provide access to the circulatory system of the patient without repeated needle punctures.

When the catheter insertion and placement steps have been concluded, one end of a tube (or "tubing set") is generally attached to the proximal end of the catheter. The opposite end of the tube is attached to a source of fluid and medication. The source of fluid is typically a bottle or bag containing the fluid required for treatment of the patient. Once attachment of the catheter to the fluid source is completed, fluids are allowed to flow through the tubing, into the catheter, and ultimately into the patient. In most situations, fluids flow through the tubing set and into the patient by means of gravity feed or using a standard infusion pump.

It will be appreciated that it is important to minimize the risk of failure when introducing an IV catheter or other medical instrument into the blood vessel of a patient. Successful introduction of an IV catheter or other medical instrument into the blood vessel of a patient requires proper positioning of the tip of the needle within the blood vessel. Introduction may fail because the needle misses the blood vessel, partially impales the blood vessel, or "blows out" the blood vessel by penetrating the opposite wall after vascular access has been achieved.

Failure is especially likely when introducing IV catheters into the veins and arteries of geriatric patients, as such patients' blood vessel walls are generally less resilient than the blood vessel walls of younger patients. As a result, a medical professional introducing an IV catheter or other medical instrument into the vein of a geriatric patient may "blow out" the vein by inadvertently penetrating the opposite wall. Failure is also likely when introducing IV catheters into the veins and arteries of neonatal patients. Such patients have small diameter blood vessels which are hard to successfully penetrate unless the medical professional uses a small diameter needle to gain venous access.

It will also be appreciated that a medical professional may wish to place an IV catheter or introducer into a blood vessel that has the same size inside diameter as the outside diameter of the catheter or introducer. However, the failure modes described above are more likely to occur where the placement of the IV catheter or introducer requires the use of a large diameter needle.

It will be further appreciated that it is important to minimize the risk of infection when introducing an IV catheter or other medical instrument into the blood vessel of a patient. The method of insertion and placement of a catheter described above involves handling of the catheter by the medical professional. Such handling creates the potential for contaminating the catheter with microorganisms, allowing the introduction of such microorganisms into the patient's circulatory system.

Attempts have been made to deal with the problems that occur when introducing an IV catheter or other medical instrument into a blood vessel. However, the proposed solutions often involve the use of large diameter needles, which, compared to smaller diameter needles, cause greater tissue damage and increase the risk of failure. Such solutions also typically involve multiple steps, including the placement of a guide wire. Procedures involving multiple steps increase both the probability of error and the danger of infection. Moreover, such solutions typically involve numerous separate components, including a needle, guide wire, and vessel dilator. The use of multiple separate components renders such solutions cumbersome. In addition, the introduction of each new component into a patient's blood vessel increases the patient's risk of infection.

In one method known as the modified Seldinger technique, a hollow thin-walled needle is inserted into the blood vessel of a patient, creating an access site, after which a guide wire is introduced through the needle. The lumen of the needle must have a large enough inside diameter such that a guide wire can be introduced through it. The needle is then removed, and a vessel dilator such as a plastic cannula is threaded into the blood vessel over the guide wire. The guide wire is removed, after which an IV catheter or other medical instrument may be inserted through the cannula and into the blood vessel. In this technique, the needle, guide wire, and vessel dilator are separate components, making this technique cumbersome. In addition, the introduction of each new component-first the needle, then the guide wire, then the cannula-into a patient's blood vessel increases the risk of failure or infection.

In a variation of this technique, a guide wire is inserted into the patient's blood vessel as described above. A tear-apart or peelable sheath cannula is then inserted into the patient's blood vessel over the guide wire. After insertion of the IV catheter or medical instrument through the lumen of the cannula, the tear-apart or peelable sheath cannula is withdrawn from the blood vessel. The cannula is then split or peeled lengthwise, allowing the user to remove it from the inserted IV catheter or medical instrument. The cannula may also include a dilator disposed within the lumen of the cannula such that the distal end of the dilator extends beyond the distal end of the cannula, allowing dilation of the access site. The dilator and cannula are inserted into the patient's blood vessel over the guide wire, after which the guide wire is removed. The dilator may be removed by withdrawing it from the access site through the cannula, after which the IV catheter or medical instrument may be inserted into the patient's blood vessel.

Another technique involves the insertion of a tear-apart or peelable sheath cannula placed over an introducer needle. The needle, with the tear-apart cannula located over the needle, is inserted into a blood vessel of a patient. The needle is then withdrawn from the tear-apart cannula and a catheter may be inserted into the patient's blood vessel through the lumen of the tear-apart cannula. However, the outer diameter of the inserted catheter can be no larger than the outer diameter of the introducer needle used.

From the foregoing, it will be appreciated that it would be an advancement in the art to provide a device that would allow a user to gain access to a patient's blood vessel without using a large diameter needle. It would also be an advancement in the art to provide such a device which would allow dilation of the access site. It would be yet another advancement to provide a device that was easy to use and that did not require the use of multiple separate components. Finally, it would be a significant advancement in the art to provide such a device which decreased the risk of infection associated with the placement and use of a catheter.

Such apparatus are disclosed and claimed herein.

BRIEF SUMMARY AND OBJECTS OF THE INVENTION

The present invention is a multiple sheath catheter using multiple stages for placing an IV catheter or other medical instrument into a blood vessel of a patient. In one embodiment, the multiple sheath catheter has the following elements: a needle, a first stage or inner catheter, a removable wing set or butterfly handle clamp, and a second stage comprising a catheter or introducer. These elements are contained in a single integrated unit.

The device utilizes a small diameter needle having a sharp tip to gain vascular access. The small diameter needle is disposed lengthwise within the first stage or inner catheter, such that the sharp tip protrudes a short distance beyond the tip of the first stage catheter. The small diameter size is the important design factor. Insertion of a small diameter needle is less likely to cause damage to a patient's blood vessel. A small diameter needle is less likely to partially impale a vein than a large diameter needle. Likewise, a small diameter needle is less likely to "blow out" a vein by penetrating the opposite wall after vascular access has been achieved. This design is based on the concept of hitting a large target with a small object.

A removable wing set or butterfly handle clamps around the needle and a first stage or inner catheter. The wing set allows the user to control the needle from a comfortable range and decreases the risk of contaminating the first stage catheter with microorganisms. When the user grasps the wing set, the wing set squeezes the first stage catheter, preventing slippage of the needle and allowing placement of the needle and first stage catheter into the patient's blood vessel.

The wing set is provided with a score line to facilitate removal from around the first stage catheter. The user removes the wing set by pinching the wings together such that the wing set breaks open along the score line.

In certain preferred embodiments, the multiple sheath catheter includes an outer tube. The outer tube protects the first stage catheter and the second stage of the device from microbiological contamination. In such embodiments, the outer tube is provided with a score line that is aligned with the score line of the wing set. Thus, when the user breaks open the wing set as described above, the outer tube also splits along its score line, allowing removal of the outer tube from the multiple sheath catheter.

The second stage of the device is slidably mounted over the first stage catheter and has a larger outer diameter than the first stage catheter. The first stage catheter serves as a guide over which the second stage of the device is threaded into the vein. It will be appreciated that a guide wire is therefore unnecessary when using the multiple sheath catheter of the present invention to insert a catheter or introducer into the blood vessel of a patient.

After introduction of the second stage of the device, the first stage catheter is removed from the blood vessel through the lumen of the second stage, leaving the second stage of the device in the vein. Thus, the first stage catheter is only inserted into a patient's blood vessel for period of time sufficient to remove the needle, remove the wing clamp, and introduce the second stage of the device. It will be appreciated that because the first stage catheter has a short indwelling time (defined as the period of time in which a device or material is in contact with tissue), the choice of material for the first stage catheter is not critical.

In certain embodiments of the multiple sheath catheter, the second stage of the device is a catheter. When using such embodiments, a medical professional may attach a drip line to the second stage of the device after removing the first stage catheter. In certain other embodiments, the second stage of the device is an introducer. When using such embodiments, a medical professional may introduce an IV catheter or other medical instrument into the patient's vein or artery through the lumen of the introducer, after which the introducer may be removed from the access site. In certain preferred embodiments, the introducer comprises a tear-apart or peelable sheath cannula, allowing removal of the introducer when the inserted IV catheter or medical instrument has proximal fittings larger than the inside diameter of the introducer.

The multiple sheath catheter of the present invention may have other optional features. For example, in certain contexts it is helpful to have a needle with a distal opening, one or more notch-like openings, and a lumen permitting fluid flow between the distal opening and notch-like openings. This allows the user to better monitor the placement of the needle; blood "flashback" through the distal opening, into the lumen of the needle, and out the notch-like openings verifies blood vessel puncture. The ability to monitor needle placement may be especially important when using small diameter needles. Thus, certain embodiments of the device optionally include such needle design.

In certain contexts, it is also desirable to minimize the leakage of blood to the outside environment during the placement of a catheter or medical instrument. Blood leakage can expose medical personnel and others to blood-borne infectious diseases such as AIDS and hepatitis. Blood leakage can contaminate equipment and supplies in the treatment area. Blood leakage may also cause unnecessary alarm on the part of the patient and other observers. In such contexts, it would be helpful to have a "bloodless" device in which a latex or polyisoprene barrier restricted blood flow from the proximal end of the first stage catheter. Following venipuncture and introduction of the first stage catheter into the blood vessel, the needle would be withdrawn through the barrier, after which the barrier would substantially re-seal. Thus, certain embodiments of the device include such a barrier.

To use the multiple sheath catheter, a medical professional punctures the blood vessel of a patient with the sharp tip of the needle, creating an access site and facilitating the introduction of part of the first stage catheter into the patient's blood vessel. The medical professional grips the multiple sheath catheter by the removable wing set. When the medical professional grasps the wing set so that the wings are brought towards each other, the wing set squeezes the first stage catheter, preventing slippage of the needle and allowing placement of the needle and first stage catheter into the patient's blood vessel. After venous or arterial access is achieved, the needle is withdrawn, leaving the first stage catheter in the vein. The medical professional next removes the wing set by splitting it open along the score line.

With the first stage catheter in the patient's vein or artery and no wing set attached to the multiple sheath catheter, the second stage of the device may now be threaded into the patient's blood vessel over the first stage catheter. The first stage catheter is then removed from the vein or artery through the lumen of the second stage of the device, leaving the second stage in the patient's blood vessel. If the second stage of the device is a catheter, the medical professional may attach a drip line. Alternatively, if the second stage of the device is an introducer, the medical professional may introduce an IV catheter or other medical instrument into the patient's blood vessel through the lumen of the introducer. The introducer may then be removed from the access site.

Thus, the multiple sheath catheter of the present invention is useful for placing an IV catheter or medical instrument into the blood vessel of a patient. The present invention allows the use of smaller diameter needles than are commonly used for venipuncture, thereby decreasing the risk of failure when introducing an IV catheter or other medical instrument into the blood vessel of a patient. The present invention also allows the user to place an IV catheter or introducer into a blood vessel that has the same size inside diameter as the outside diameter of the catheter or introducer. The present invention is easy to use and does not require the use of multiple components; rather, the needle, first stage catheter, removable wing set, and second stage catheter or introducer are provided as a single integrated device. The present invention further minimizes the risk of infection associated with the insertion and placement of catheters. These and other objects of the present invention will become more fully apparent by examination of the following description of the preferred embodiments and the accompanying drawings.

BRIEF DESCRIPTION OF THE DRAWINGS

In order to more fully understand the manner in which the above-recited advantages and objects of the invention are obtained, a more particular description of the invention briefly described above will be rendered by reference to specific embodiments thereof which are illustrated in the appended drawings. The embodiments illustrated in the drawings are merely illustrative.

DETAILED DESCRIPTION OF THE PREFERRED EMBODIMENTS

Figure 1:
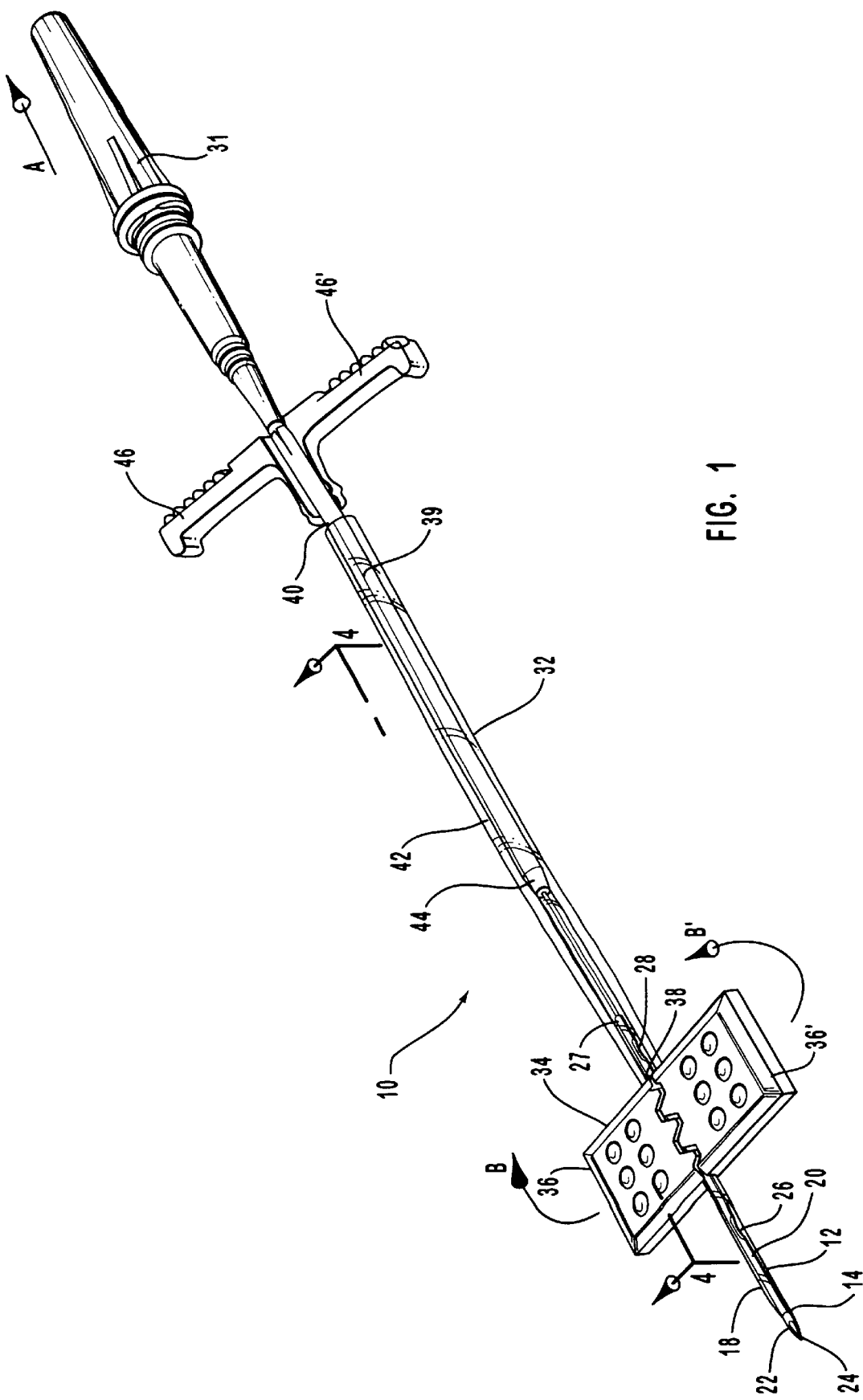
FIG. 1 is a perspective view of one embodiment of the present invention.

The present invention can be best understood by reference to the drawings in which like parts are designated with like numerals throughout. One embodiment of the multiple sheath catheter of the present invention is generally designated 10 in FIG. 1. As mentioned above, the multiple sheath catheter 10 allows for the placement of a catheter or introducer into the blood vessel of a patient. As illustrated in FIG. 1, the multiple sheath catheter 10 includes a first stage catheter 12. The first stage catheter 12 includes a distal end 14, a proximal end 16, and an internal lumen 18 between the distal end 14 and the proximal end 16.

A needle 20 having a sharpened end 22 is disposed lengthwise within the internal lumen 18 of the first stage catheter 12, such that the sharpened end 22 of the needle protrudes a short distance beyond the distal end 14 of the first stage catheter 12. The sharpened end 22 allows a medical professional to puncture the blood vessel of a patient, creating an access site and facilitating the introduction of the distal end 14 of the first stage catheter 12 into the blood vessel. The distal end 14 of the first stage catheter 12 is tapered, allowing dilation of the access site and facilitating the introduction of at least part of the first stage catheter 12 into the patient's blood vessel.

The sharpened end 22 of needle 20 includes a distal opening 24. The needle 20 also includes a first notch-like opening 26, and a second notch-like opening 28. As shown in cross section in FIG. 4, the needle 20 also includes a lumen 30, permitting fluid to flow between the distal opening 24, the first notch-like opening 26, and the second notch-like opening 28. The first notch-like opening 26 and second notch-like opening 28 allow the user to monitor placement of the needle 20 by watching for blood flashback out of the notch-like openings 26 and 28 and into the lumen 18 of the first stage catheter 12. The first notch-like opening 26 is located distal to a removable wing set 34, described below, which allows the user to grip the multiple sheath catheter 10 by the wing set 34 while monitoring for blood flashback out of the first notch-like opening 26. The second notch-like opening 28 is located proximal to the removable wing set 34.

Figure 4:
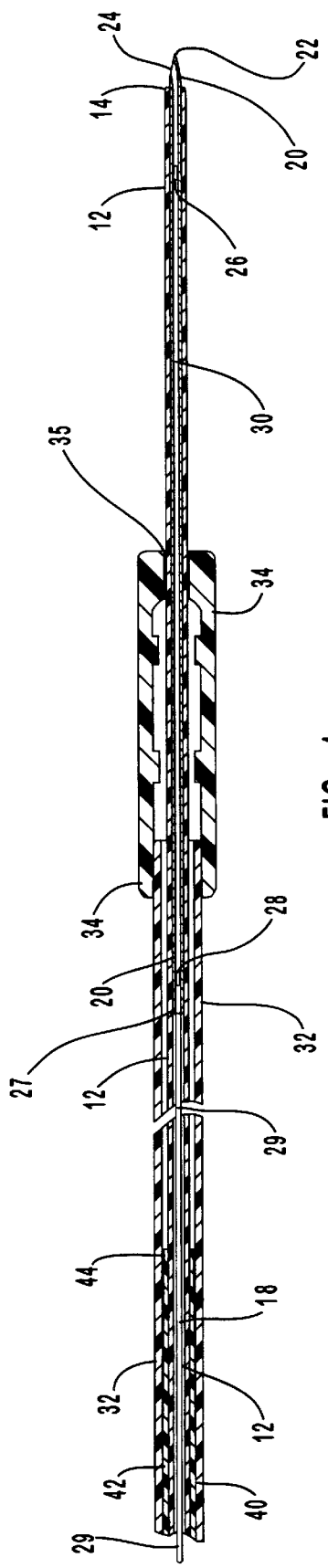
FIG. 4 is a fragmented side cross-sectional view taken on line 4—4 of FIG. 1.

As shown in FIG. 4, the needle 20 is provided with a proximal end 27 attached to a wire 29 disposed within the internal lumen 18 of the first stage catheter 12. The wire 29 extends coaxially through the internal lumen 18 of the first stage catheter 12 and is attached to a finger grip 31 (shown in FIG. 1), such that after the introduction of at least part of the first stage catheter 12 into the blood vessel, the needle 20 may be withdrawn from the access site by pulling the finger grip 31 in the direction indicated by arrow A (shown in FIG. 1), minimizing the risk of injury to the blood vessel.

Figure 2:
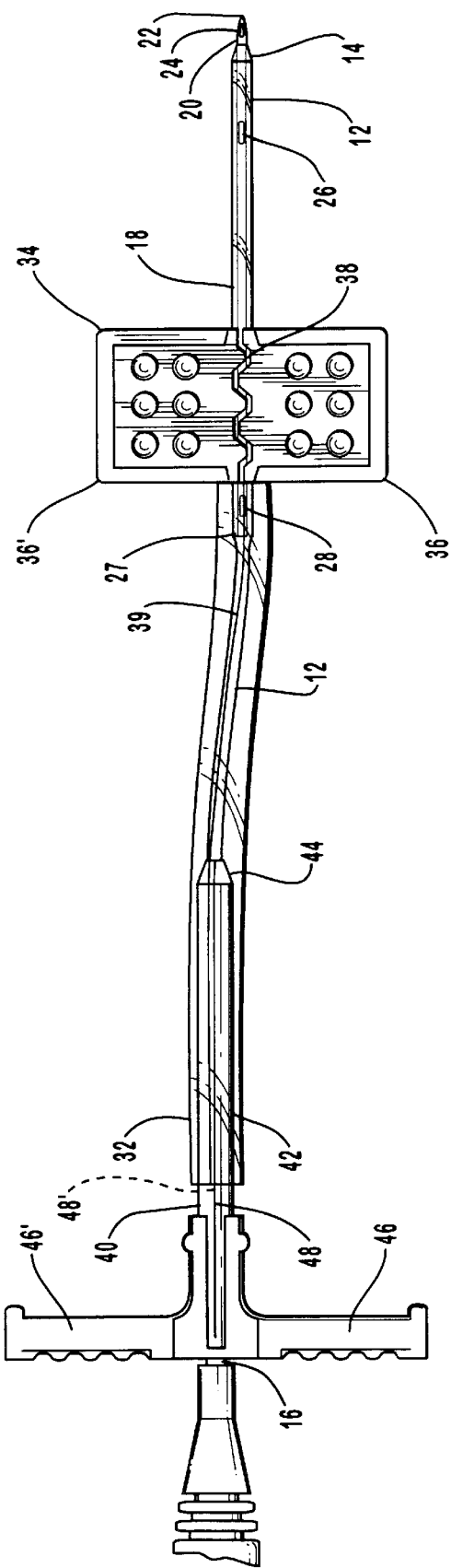
FIG. 2 is a fragmented plan view of the embodiment of the device illustrated in FIG. 1.
Figure 3:
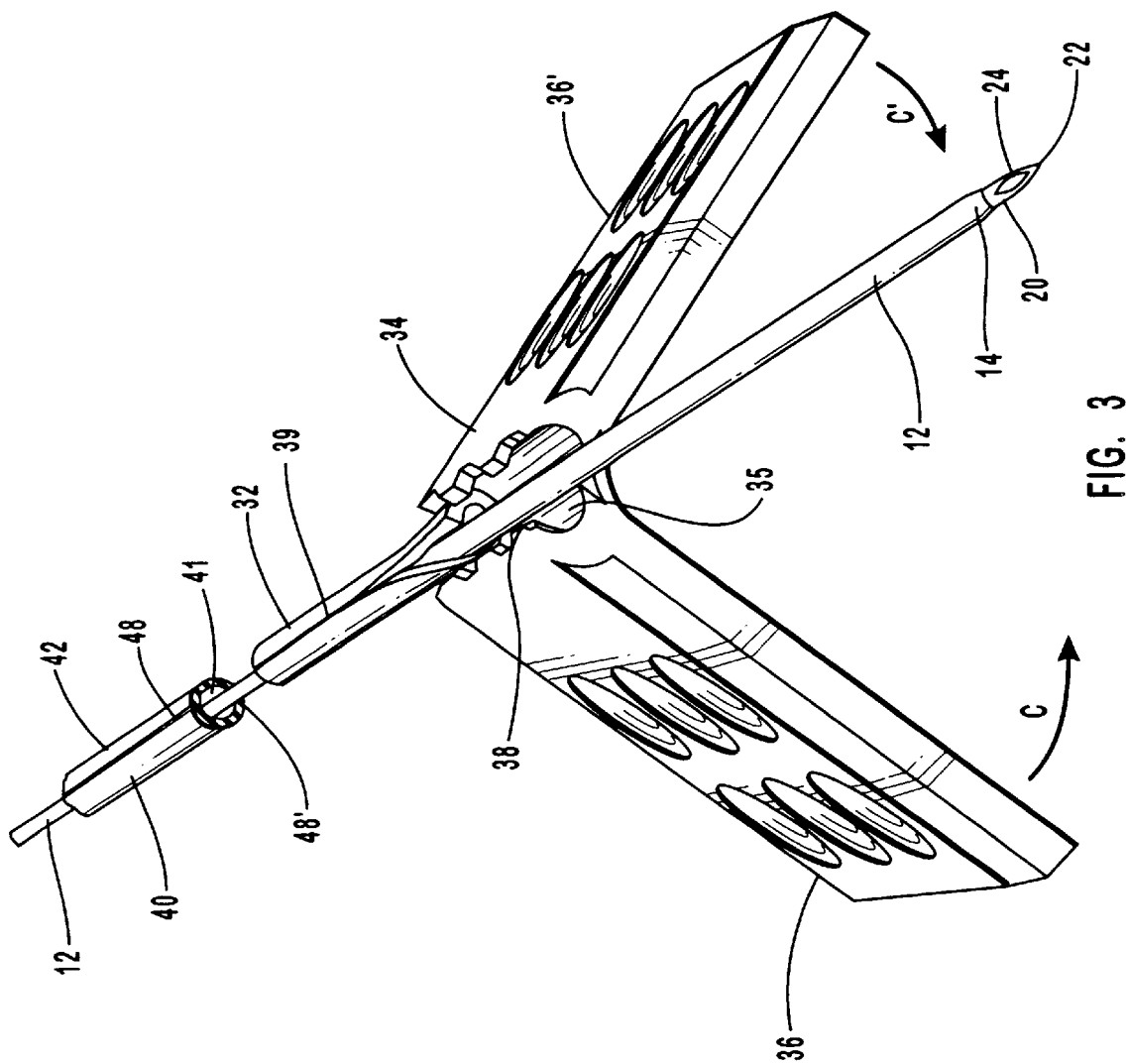
FIG. 3 is a fragmented perspective view illustrating the removable wing set and outer tube being removed from the multiple sheath catheter.

The multiple sheath catheter 10 includes a removable wing set 34. As shown in FIG. 1, the removable wing set 34 includes a pair of wings 36 and 36'. As illustrated in FIG. 2, the wings 36 and 36' are respectively on substantially opposite sides of the multiple sheath catheter 10. As shown in FIG. 3, the removable wing set 34 includes a bore 35 disposed about the inner catheter 12. When wings 36 and 36' are brought towards each other in the direction of arrows B and B' (shown in FIG. 1), the first stage catheter is squeezed by the removable wing set 34. Thus, the first stage catheter 12 grips the needle 20, preventing slippage of the needle 20, facilitating the introduction of the first stage catheter 12 into the blood vessel. Moreover, the wings 36 and 36' allow the medical professional to grip the multiple sheath catheter 10 without touching and thereby compromising the sterility of either the first stage catheter 12 or the second stage introducer 40.

In certain preferred embodiments, the multiple sheath catheter also includes an outer tube 32, as shown in FIG. 1.

The outer tube 32 is disposed about the first stage catheter 12 and second stage introducer 40. The outer tube 32 allows the medical professional to handle the multiple sheath catheter 10 without touching and thereby compromising the sterility of either the first stage catheter 12 or the second stage introducer 40. The removable wing set 34 is flexibly mounted to the outer tube 32.

The removable wing set 34 is provided with a score line 38 disposed intermediate between the wings 36 and 36'. Likewise, the outer tube 32 is provided with a score line 39 that is generally collinear with the score line 38 on the removable wing set 34. After the introduction of the distal end 14 of the first stage catheter 12 into the blood vessel, the removable wing set 34 and outer tube 32 may be removed from the multiple sheath catheter 10. As shown in FIG. 3, when wings 36 and 36' are brought towards each other in the direction of arrows C and C', the removable wing set 34 splits along the score line 38 and the outer tube 32 splits along the score line 39, allowing removal of the removable wing set 32 and outer tube 32 from the multiple sheath catheter 10.

Referring once again to FIG. 1, disposed about at least part of the first stage catheter 12 is the second stage introducer 40, which has a lumen 41 and a tubular portion 42 of approximately uniform thickness and diameter except at its distal end 44. At the distal end 44 of the second stage introducer 40, there is a slight taper to create a snug fit with the inner catheter 12 and also to allow dilation of the access site, facilitating the introduction of the second stage introducer 40 into the blood vessel.

The second stage introducer 40 is provided with a pair of tabs 46 and 46' and a pair of diametrically opposed score lines 48 and 48' disposed intermediate between the tabs 46 and 46', such that the application of opposed radial forces to the tabs 46 and 46' results in longitudinal splitting of the second stage introducer 40 along the opposed score lines 48 and 48'. This feature allows removal of the second stage introducer 40 from an IV catheter or other medical device inserted into the patient's blood vessel through the lumen 41 of the second stage introducer 40.

In operation, the user grips the multiple sheath catheter 10 by the removable wing set 34. When the user pinches the wings 36 and 36' towards each other in the direction of arrows B and B' (shown in FIG. 1), the first stage catheter is squeezed by the removable wing set 34. At this point the first stage catheter 12 grips the needle 20, preventing slippage of the needle 20 within the lumen 18 of the first stage catheter 12. This allows the user to puncture the blood vessel of a patient with the sharpened end 22 of the needle 20 and facilitates the introduction of at least part of the distal end 14 of the first stage catheter 12 into the patient's blood vessel. The notch-like openings 26 and 28 allow the user to monitor the placement of the needle 20. Blood flashback through the distal opening 24, into the lumen 30 (shown in FIG. 4) of the needle 20, and out the notch-like openings 26 and 28 verifies blood vessel puncture.

After proper placement of the needle 20 and the distal end 14 of the first stage catheter 12 into the patient's blood vessel, the needle 20 is withdrawn to prevent inadvertent damage to the blood vessel. The user withdraws the needle 20 by pulling on finger grip 31, which is attached by wire 29 (shown in FIG. 4) to the proximal end 27 of the needle 20, in the direction of arrow A (shown in FIG. 1). This leaves the distal end 14 of the first stage catheter 12 in the patient's blood vessel.

The user may then remove the removable wing set 34 and outer tube 32 from the multiple sheath catheter 10 by bringing wings 36 and 36' towards each other in the direction of arrows C and C' (shown in FIG. 3). This causes the removable wing set 34 to split along score line 38. Likewise, this action causes the outer tube 32 to split open along score line 39. After removal of the removable wing set 34 and outer tube 32, the second stage introducer 40 is inserted into the patient's blood vessel over the inner catheter 12, dilating the access site. The elasticity of the skin around the access site forms a seal, minimizing blood leakage. The first stage catheter 12 may then be removed from the access site through the lumen 41 of the second stage introducer 40. A medical device such as an intravenous (IV) catheter may then be threaded into the blood vessel through the lumen 41 of the introducer 40. The user may remove the introducer 40 from the blood vessel by sliding it along the inserted medical device. The second stage introducer 40 may then be removed from the inserted IV catheter by applying opposed radial forces to tabs 46 and 46', resulting in the longitudinal splitting of the second stage introducer 40 along opposed score lines 48 and 48'.

In summary, the present invention provides a device for use in placing an IV catheter or other medical instrument into the blood vessel of a patient. The present invention provides a device which increases the placement success rate because the needle is of a smaller diameter than is commonly used for venipuncture. The multiple sheath catheter of the present invention can also be used without significant modification of conventional catheters, tubing sets and the like. The present invention does not require the use of multiple components or a guide wire and is easy to use. The present invention also provides a device which minimizes the risk of infection associated with the insertion and placement of catheters.

The invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed and desired to be secured by Letters Patent is:

1. A multiple sheath catheter comprising:
    a first stage catheter comprising a distal end for introducing into a blood vessel, a proximal end, and an internal lumen between the distal and proximal ends;
    a needle comprising a sharp tip, the needle being disposed lengthwise within the lumen of the first stage catheter such that the sharp tip projects beyond the distal end of the first stage catheter;
    a second stage cannula comprising a lumen, wherein the first stage catheter is disposed lengthwise within the lumen of the second stage cannula; and
    gripping means for squeezing the first stage catheter such that the needle disposed within the lumen of the first stage catheter can be gripped by the first stage catheter wherein the gripping means comprises a wing set flexibly mounted to the first stage catheter, the wing set comprising two diametrically opposed wings, wherein the wing set is adapted to squeeze the first stage catheter by bringing the two diametrically opposed wings towards each other.

2. A multiple sheath catheter as defined in claim 1, wherein the wing set further comprises a score line such that the wing set may be removed from the first stage catheter.

3. A multiple sheath catheter comprising:
a first stage catheter comprising a distal end for introducing into a blood vessel, a proximal end, and an internal lumen between the distal and proximal ends;
a needle comprising a sharp tip, the needle being disposed lengthwise within the lumen of the first stage catheter such that the sharp tip projects beyond the distal end of the first stage catheter;
a second stage cannula comprising a lumen, wherein the first stage catheter is disposed lengthwise within the lumen of the second stage cannula; and
gripping means for squeezing the first stage catheter such that the needle disposed within the lumen of the first stage catheter can be gripped by the first stage catheter wherein the gripping means comprises a wing set flexibly mounted to an outer tube disposed about the first stage catheter, the wing set comprising two diametrically opposed wings, wherein the wing set is adapted to squeeze the first stage catheter by bringing the two diametrically opposed wings towards each other.

4. A multiple sheath catheter as defined in claim 3, wherein the wing set further comprises a score line and the outer tube comprises a score line, such that the wing set and outer tube may be removed from the first stage catheter.

5. A multiple sheath catheter comprising:
a first stage catheter comprising a distal end for introducing into a blood vessel, a proximal end, and an internal lumen between the distal and proximal ends;
a needle comprising a sharp tip, the needle being disposed lengthwise within the lumen of the first stage catheter such that the sharp tip projects beyond the distal end of the first stage catheter;
a second stage cannula comprising a lumen, wherein the first stage catheter is disposed lengthwise within the lumen of the second stage cannula; and
gripping means for squeezing the first stage catheter such that the needle disposed within the lumen of the first stage catheter can be gripped by the first stage catheter wherein the needle further comprises a distal opening, a first notch-like opening, a second notch-like opening, and a lumen, such that fluid may flow between the distal opening, the first notch-like opening, and the second notch-like opening.

6. A multiple sheath catheter comprising:
a first stage catheter comprising a distal end for introducing into a blood vessel, a proximal end, and an internal lumen between the distal and proximal ends;
a needle comprising a sharp tip, the needle being disposed lengthwise within the lumen of the first stage catheter such that the sharp tip projects beyond the distal end of the first stage catheter;
a second stage catheter comprising a lumen, wherein the first stage catheter is disposed lengthwise within the lumen of the second stage catheter; and
gripping means for squeezing the first stage catheter such that the needle disposed within the lumen of the first stage catheter cab be gripped by the first stage catheter, wherein the gripping means comprises a wing set flexibly mounted to the first stage catheter, the wing set comprising two diametrically opposed wings, wherein the wing set is adapted to squeeze the first stage catheter by bringing the two diametrically opposed wings towards each other.

7. A multiple sheath catheter as defined in claim 6, wherein the wing set further comprises a score line such that the wing set may be removed from the first stage catheter.

8. A multiple sheath catheter comprising:
a first stage catheter comprising a distal end for introducing into a blood vessel, a proximal end, and an internal lumen between the distal and proximal ends;
a needle comprising a sharp tip, the needle being disposed lengthwise within the lumen of the first stage catheter such that the sharp tip projects beyond the distal end of the first stage catheter;
a second stage catheter comprising a lumen, wherein the first stage catheter is disposed lengthwise within the lumen of the second stage catheter; and
gripping means for squeezing the first stage catheter such that the needle disposed within the lumen of the first stage catheter cab be gripped by the first stage catheter, wherein the gripping means comprises a wing set flexibly mounted to an outer tube disposed about the first stage catheter, the wing set comprising two diametrically opposed wings, wherein the wing set is adapted to squeeze the first stage catheter by bringing the two diametrically opposed wings towards each other.

9. A multiple sheath catheter as defined in claim 8, wherein the wing set further comprises a score line and the outer tube comprises a score line, such that the wing set and outer tube may be removed from the first stage catheter.

10. A multiple sheath catheter comprising:
a first stage catheter comprising a distal end for introducing into a blood vessel, a proximal end, and an internal lumen between the distal and proximal ends;
a needle comprising a sharp tip, the needle being disposed lengthwise within the lumen of the first stage catheter such that the sharp tip projects beyond the distal end of the first stage catheter;
a second stage catheter comprising a lumen, wherein the first stage catheter is disposed lengthwise within the lumen of the second stage catheter; and
gripping means for squeezing the first stage catheter such that the needle disposed within the lumen of the first stage catheter cab be gripped by the first stage catheter, wherein the needle further comprises a distal opening, a first notch-like opening, a second notch-like opening, and a lumen, such that fluid may flow between the distal opening, the first notch-like opening, and the second notch-like opening.

11. A method of introducing an intravenous catheter into a blood vessel comprising the steps of:
gaining access to the blood vessel by means of a needle, said needle comprising a sharp tip and being disposed lengthwise within a first stage catheter having a proximal end and a distal end and an internal lumen between the proximal and distal ends, such that the sharp tip of the needle projects beyond the distal end of the first stage catheter;
introducing the distal end of the first stage catheter into the blood vessel;
removing the needle from the blood vessel without removing the first stage catheter;
advancing a second stage introducer over the first stage catheter;
removing the first stage catheter from the blood vessel;
introducing an intravenous catheter through the second stage introducer and into the blood vessel;
removing the second stage introducer from the blood vessel, leaving the intravenous catheter in place.

12. A method of introducing an intravenous catheter into a blood vessel as in claim 11, wherein the first stage catheter further comprises a wing set, said wing set being used to grip the first stage catheter.

13. A method of introducing an intravenous catheter into a blood vessel as in claim 11, wherein the needle is notched.

14. A method of introducing an intravenous catheter into a blood vessel comprising the steps of:

gaining access to the blood vessel by means of a needle, said needle comprising a sharp tip and being disposed lengthwise in a first stage catheter having a proximal end and a distal end and an internal lumen between the proximal and distal ends, such that the sharp tip of the needle projects beyond the distal end of the first stage catheter;

introducing the distal end of the first stage catheter into the blood vessel;

removing the needle from the blood vessel without removing the first stage catheter;

advancing an intravenous catheter over the first stage catheter;

removing the first stage catheter from the blood vessel.

15. A method of introducing an intravenous catheter into a blood vessel as in claim 14 wherein the first stage catheter further comprises a wing set, said wing set being used to grip the first stage catheter.

16. A method of introducing an intravenous catheter into a blood vessel as in claim 14, wherein the needle is notched.

* * * * *